US009418186B2

(12) United States Patent
Sundaram et al.

(10) Patent No.: US 9,418,186 B2
(45) Date of Patent: Aug. 16, 2016

(54) ASSESSMENT OF SOLUTE PARTITIONING IN CRUDE OILS

(71) Applicants: Narasimhan Sundaram, Fairfax, VA (US); Bryan M Knickerbocker, Centreville, VA (US); Steven Wong, Spring, TX (US)

(72) Inventors: Narasimhan Sundaram, Fairfax, VA (US); Bryan M Knickerbocker, Centreville, VA (US); Steven Wong, Spring, TX (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 654 days.

(21) Appl. No.: 13/895,635

(22) Filed: May 16, 2013

(65) Prior Publication Data

US 2013/0317793 A1 Nov. 28, 2013

Related U.S. Application Data

(60) Provisional application No. 61/560,679, filed on May 23, 2012.

(51) Int. Cl.
| | |
|---|---|
| *G06F 7/60* | (2006.01) |
| *G06F 17/50* | (2006.01) |
| *G06F 19/00* | (2011.01) |
| *C10G 75/02* | (2006.01) |

(52) U.S. Cl.
CPC ............ *G06F 17/5018* (2013.01); *C10G 75/02* (2013.01); *G06F 19/704* (2013.01)

(58) Field of Classification Search
CPC ... G06F 17/5018; G06F 19/704; C10G 75/02; C09K 8/52; C09K 2208/22; C09K 8/524; C09K 8/528; C02F 5/12; C02F 5/14; C07C 7/20; Y10T 137/0391
USPC ................................................ 703/12; 702/2
See application file for complete search history.

(56) References Cited

U.S. PATENT DOCUMENTS

| | | | |
|---|---|---|---|
| 5,500,138 | A | 3/1996 | Bacon et al. |
| 6,379,612 | B1 | 4/2002 | Reizer et al. |
| 6,849,591 | B1 | 2/2005 | Boeckh et al. |
| 7,160,507 | B2 | 1/2007 | Dahlmann et al. |
| 7,341,674 | B1 | 3/2008 | Trinh et al. |
| 7,348,451 | B2 | 3/2008 | Dahlmann et al. |

FOREIGN PATENT DOCUMENTS

WO 2007107502 A1 9/2007

OTHER PUBLICATIONS

Leo (Partition Coefficients and Their Uses, Chemical Reviews, vol. 71, No. 6, Dec. 1971).*

(Continued)

*Primary Examiner* — Kamini S Shah
*Assistant Examiner* — Scott S Cook
(74) *Attorney, Agent, or Firm* — Larry E. Carter; Glenn T. Barrett; Andrew T. Ward (57) ABSTRACT

Partition coefficients for solutes in solvent-water systems are estimated based on corresponding values for the octanol-water system. The estimation of the partition coefficient includes correction factors based on the nature of the solute and the solvent. Petroleum fractions are an example of a suitable solvent for which a partition coefficient can be estimated, although other types of solvents can be used in developing a model for use in the estimation.

18 Claims, 5 Drawing Sheets

(56) References Cited

OTHER PUBLICATIONS

Octanol_Water_2010.pdf CHEM 311 http://web.archive.org/web/20111101204401/http://web.viu.ca/krogh/chem331/chem_331_h . . . Jan. 5, 2016 Nov. 2011.*

Aizawa (Emission Scenario Document on Chemicals used in Oil Well Production, OECD Environmental, Health and Safety Publications No. 31 Series on Emission Scenario Documents, Environmental Directorate Joint Meeting of the Chemicals Committee and the Working Party on Chemicals, Pesticides and Biotechnology, ENV/JM/MONO(2012)7, Mar. 19, 2012).*

Ramsden_2000.pdf, A-Level Chemistry, Fourth Edition, 2000.*

Leo_1970.pdf Leo, A., Linear Free-Energy Relationships between Partitioning Solvent Systems, J. Org. Chem., vol. 36, No. 11, 1971.*

US_EPA_2011.pdf Waxes and Related Materials, High Production Volume (HPV) Chemical Challenge Program, Category Analysis and Hazard Characterization, The Petroleum HPV Testing Group, Jan. 21, 2011.*

Knaepen et al., "Experimental Aspects of Partitioning Tracer Tests for Residual Oil Saturation Determination With FIA-Based Laboratory Equipment", SPE Reservoir Engineering, May 1990, pp. 239-244.

Leo et al., "Linear Free-Energy Relationships between Partitioning Solvent Systems", Journal of Organic Chemistry, vol. 36, No. 11, 1971, pp. 1539-1544.

Leo et al., "Partition Coefficients and Their Uses", Chemical Reviews, vol. 71, No. 6, Dec. 1971, pp. 525-616.

* cited by examiner

ASSESSMENT OF SOLUTE PARTITIONING IN CRUDE OILS

FIELD OF THE INVENTION

This invention provides methods for assessing the partitioning of solutes between oil fractions and water.

BACKGROUND OF THE INVENTION

Petroleum processing and extraction typically results in the interaction of various chemicals with a crude oil, crude oil fraction, pipelineable fraction, or refinery stream. Due to the large number of crude oil compositions and further variations introduced by processing of crude oils, a vast number of combinations of petroleum fraction plus additive are possible. Performing a detailed analysis of each possible combination is impractical for a variety of reasons. As a result, it is desirable to have methods which can allow for prediction of the properties and/or outcomes when a substance is added to a petroleum fraction or refinery stream.

Previous journal articles describes prediction of partition coefficients of organic solutes between water and immiscible solvents. (See Leo et al., Chem. Rev., Vol. 71, pg 525 (1971) or Journal of Organic Chemistry, Vol. 36, pg 1539 (1970).) The article describes efforts to develop a linear correlation between partition coefficients for the octanol-water system and partition coefficients for various organic solvents with water. The organic solvents in the journal article are solvents having ten carbons or less.

SUMMARY OF THE INVENTION

In one aspect, a method is provided for predicting a partition coefficient for a solute between a petroleum fraction and water. The method includes selecting a solute class for a solute; determining a solubility constant of water in a petroleum fraction; calculating a solute activity factor based on the solubility constant of water in the petroleum fraction, a solubility constant of the solute in water, a partition coefficient for the solute in octanol and water, and the solute class; and predicting a partition coefficient for the solute in the petroleum fraction and water based on the partition coefficient for the solute in octanol and water, the solute activity factor, and a scaling factor based on the solubility constant of water in the petroleum fraction.

In another aspect, a method is provided for predicting a partition coefficient for a solute between a solvent and water. The method includes identifying a plurality of solute classes; fitting parameters for determining a slope in a linear or quasi-linear relationship between a partition coefficient in a solvent and water and a corresponding partition coefficient in octanol and water, the parameters for determining the slope corresponding to coefficients in a polynomial expression, the fitting of parameters being based on a plurality of solvent-water systems; selecting a solute class for a solute; determining a solubility constant of water in a solvent, the solvent being different from solvents in the plurality of solvent-water systems; calculating a solute activity factor based on the solubility constant of water in the solvent, a solubility constant of the solute in water, a partition coefficient for the solute in octanol and water, and the solute class; and predicting a partition coefficient for the solute in the solvent and water based on the partition coefficient for the solute in octanol and water, the solute activity factor, and a scaling factor based on the solubility constant of water in the solvent.

DETAILED DESCRIPTION OF THE EMBODIMENTS

Overview

In various embodiments, methods are provided for predicting the partition coefficient of a solute between a petroleum fraction and water. Examples of solutes include scale inhibitors, corrosion inhibitors, gas hydrate formation inhibitor, or other types of compounds that may be added to a petroleum fraction during extraction, transport, or processing. The methods allow for prediction of the partition coefficient using values that can be determined either in advance or that are relatively easy to determine on site at a refinery or extraction facility.

The method described herein allows the existing octanol-water partition database to be used to provide information regarding partitioning between water and a petroleum fraction or other solvent. The use of the existing octanol-water partition database is enabled in part by the discovery that the partition coefficient for a solute in water versus a petroleum fraction can be correlated with the partition coefficient for the solute in water and octanol and with the solubility of water in the petroleum fraction. Based on this discovery, determining the solubility of water in a petroleum fraction can allow for estimation or prediction of a partition coefficient for a solute between water and the petroleum fraction if an octanol-water partition coefficient is available.

The improved estimates of partition coefficient provided according to the invention are based in part on the recognition that solutes can be divided into a plurality of classes. This allows a family of linear or quasi-linear relationships to be developed between octanol-water partition coefficients and petroleum fraction-water (or other solvent-water) partition coefficients. The classes are not dependent on whether the petroleum fraction shares a common functional group with octanol. Instead, the classes can be defined based on structure and/or properties of the solute that is being partitioned.

It is noted that the estimated partition coefficient provided according to the invention may provide only a qualitative assessment of partitioning, as opposed to a quantitative result. However, a qualitative assessment can still provide many advantages. In a commercial setting, it is often relevant to know the order of magnitude of solute concentration resulting from partitioning between a petroleum fraction and water. For example, such an order of magnitude estimate can allow for determination of whether a given additive will be present in the petroleum fraction in a concentration that is detrimental to a downstream process, or whether the concentration will be low enough that a further investigation is not needed. Similarly, an order of magnitude estimate can indicate whether a substantial portion of an additive is being dissolved in water adjacent to an extraction site, or whether the additive is primarily being extracted along with the petroleum fraction.

Definitions

In this discussion, a petroleum fraction is defined as an oil stream containing at least 50 wt % of oil derived from a mineral source. Such a definition includes whole or partial crude oils either prior to or after extraction. The definition also includes oil streams derived from a whole or partial crude after one or more distillation, blending, and/or processing steps. A petroleum fraction as defined herein can optionally include one or more additives that are added to the petroleum fraction to facilitate extraction, transport, or processing of the petroleum fraction. Preferably, the petroleum fraction contains at least 75 wt % of oil derived from a mineral source, and more preferably at least 90%. For a petroleum fraction containing less than 100 wt % of oil derived from a mineral source, a portion of the non-mineral oil content can optionally correspond to oil derived from a biological source. In some embodiments, a petroleum fraction is defined to consist essentially of oil derived from a mineral source. A petroleum fraction that consists essentially of oil derived from a mineral source excludes petroleum fractions that contain oil derived from a biological source, such as oils derived from plants, animals, or algae. A petroleum fraction that consists essentially of oil derived from a mineral source includes oils that have been modified by processing, such as hydroprocessing, distillation, blending, and/or cracking. Note that modification of a petroleum fraction includes modification of the chemical composition, such as increasing or lowering the hydrogen content of the petroleum fraction. A petroleum fraction that consists essentially of oil derived from a mineral source can also include additives that are introduced into the oil in order to facilitate extraction, transport, or processing of the oil. For a petroleum fraction that consists essentially of oil derived from a mineral source, the source or derivation of any additives to the mineral oil is not limited to mineral oil sources. Examples of additives include scale inhibitors, corrosion inhibitors, compounds for preventing or reducing hydrate formation, and/or other compounds for facilitating extraction or transport of oils. In a petroleum fraction that consists essentially of oil derived from a mineral source, such additives can be present in the petroleum fraction in a typical amount that results from use of such additives in a conventional extraction or transport process.

A scale inhibitor is a composition suitable for use in inhibiting oil field scale formation. Examples of conventional scale inhibitors include phosphonates, acrylic co-polymers and terpolymers, polyacrylic acid, phosphinocarboxylic acid, and phosphate esters. Such scale inhibitors can optionally be mixed with amines.

A corrosion inhibitor is a composition suitable for use in reducing or preventing corrosion of equipment used in recovery and transport of petroleum fractions. Examples of corrosion inhibitors include quaternary ammonium compounds, such as alkylammonium compounds or alkoxylated alkylammonium compounds.

A gas hydrate inhibitor is a composition suitable for use in reducing or preventing formation and/or agglomeration of gas hydrates during oil extraction and transport. Examples of gas hydrate inhibitors include alcohols and glycols, ammonium compounds, amines and diamines, and hydroxycarbylamides.

Partition Coefficient

A partition coefficient is a value related to how a solute will be divided between intermixed liquid phases at equilibrium. A common reference system for describing a partition coefficient is water and octanol. Water and octanol have limited miscibility, so a mixture of water and octanol will typically form separate water and octanol phases. If a solute is introduced into the mixture of water and octanol, the partition coefficient describes the amount of the solute that will be dissolved in the water phase versus the amount that will be dissolved in the octanol phase.

A formal definition for the partition coefficient of a solute in a solvent and water is $$P_{solute}(\text{solvent, water}) = \frac{[\text{solute}]_{solvent}}{[\text{solute}]_{water}} \quad (1)$$

In the above equation, $[\text{solute}]_{phase}$ refers to the concentration in solution of the solute in the given phase (such as octanol, water, or a petroleum fraction) at equilibrium. When referencing partition coefficient values, a logarithm of the partition coefficient value is often used, such as log $P_{solute}$(solvent,water).

Octanol and water represent a commonly used solvent pair for studying the partitioning of a solute between phases. As a result, the coefficient $P_{solute}$(octanol,water) has been determined for a wide variety of compounds.

Conventionally, it has been postulated that partition coefficients for various solvents and water may be related to each other in a linear manner, so long as the various solvents have similar functional groups. In a laboratory setting, this provides a way to extend the value of databases such as the octanol-water database by allowing partition coefficients to be predicted for a broader range of solvents. Unfortunately, petroleum fractions typically contain a mixture of compounds, and the number and nature of the functional groups in a petroleum fraction may not be readily available without extensive investigation.

In various embodiments, methods are provided for using an octanol-water partition coefficient as the basis for determining a partition coefficient for a solute in a petroleum fraction and water. Based on these methods, a series of linear relationships (or quasi-linear relationships) can be determined between octanol-water partition coefficients and petroleum-fraction water partition coefficients. It has been discovered that the linear relationship to be used for a given solute is dependent on the nature of the functional groups in the solute. It has further been discovered that a scaling factor or slope for the linear relationship can be determined based on the solubility of water in the petroleum fraction. This allows a partition coefficient for a solute in a petroleum fraction and water to be determined without having to directly measure properties of the solute in the petroleum fraction. Instead, the partition coefficient can be estimated based on more commonly available properties, such as the octanol-water partition coefficient and the solubility of water in the petroleum fraction.

In order to improve the estimation of a partition coefficient based on a corresponding octanol-water coefficient, the estimation of a partition coefficient for a solute relative to a petroleum fraction and water can be modified based on the nature of the petroleum fraction and the nature of the solute. In various embodiments, the nature of the petroleum fraction can be captured as part of a scaling factor and/or slope for a linear relationship between an octanol-water partition coefficient and a corresponding petroleum fraction-water partition coefficient. The nature of the solute can be captured by selecting an appropriate linear relationship based on a solute class, and by incorporating a solute activity factor as an additional scaling factor.

Solute Classes and Solute Activity Factor

Petroleum fraction-water partition coefficients generally have a linear or quasi-linear relationship to corresponding octanol-water partition coefficients, but the same linear relationship does not hold for all solutes. Instead, dividing solutes into at least three classes of solutes is beneficial for estimating a petroleum fraction-water partition coefficient using a linear or quasi-linear relationship to an octanol-water partition coefficient. Without the recognition of multiple classes of solutes, the linear or quasi-linear relationship can appear to break down across a general group of solutes.

One suitable method for classifying solutes is to group solutes into a plurality of solute classes, such as three solute classes. The classification of the solutes is based on the chemical structure of the solutes. In this option, the first class of solutes corresponds to solutes containing either an acidic functional group, a sulfur atom, or a hydroxyl (i.e., —OH group). Examples of acidic functional groups include carboxylic acid groups and other groups that cause a 0.1 mole/liter solution of the solute in water to have a pH of less than 6.0. A second class of solutes corresponds to solutes containing one or more nitrogen atoms. In a preferred embodiment, if the solute contains nitrogen, the solute is placed in the second class of solutes. If a solute does not correspond to either the first class or the second class, the solute is classified as belonging to the third class of solutes. It is understood that the above classification scheme is not unique, and that additional and/or different classes for solutes could be used to define a family of linear or quasi-linear relationships between petroleum fraction-water coefficients and octanol-water coefficients.

In addition to determining a class for a solute, a solute activity factor can also be determined for a solute. A solute activity factor is a scaling value that allows for correction of the relationship between an octanol-water coefficient and a petroleum fraction-water partition coefficient on a per solute basis. The solute activity factor can be based on a correlation value. One suitable form for the correlation value is $$C_{activity} = \frac{\ln\left(\frac{K_{solute}(\text{water})}{K_{water}(\text{solvent})}\right)}{\log P_{solute}(\text{octanol, water})} \quad (2)$$

In equation (2), $C_{activity}$ is the correlation value, $K_{solute}$(water) corresponds to the solubility constant of a solute in water, $K_{water}$(solvent) corresponds to the solubility constant of water in a solvent (such as a petroleum fraction), and $P_{solute}$(octanol,water) is a partition coefficient for a solute in octanol and water as described above. In equation (2), the correlation value can be determined from values that are either likely to be available or that can be readily obtained by estimation or measurement. In particular, detailed characterization of the composition of the petroleum fraction is not required.

Based on the correlation value, the solute activity factor can be defined on a class dependent basis. For example, if the classes are defined as nitrogen-containing solutes, acidic or sulfur-containing solutes, and other solutes, the solute activity factor can be defined for each class as: $\lambda_{Nitrogen}=\alpha_1 * C_{activity}$; $\lambda_{acid}=\alpha_2 * C_{activity}$; and $\alpha_{Other}=\alpha_3 * C_{activity}$. In one example of a determination of class correlation values, the α value for the nitrogen class was −5.4, the α value for the acid/sulfur class was 1.0, and the α value for the other class was 4.3. Optionally, the definition for a solute activity factor can also include a slope. For example, the solute activity factor for the nitrogen class can be $\lambda_{Nitrogen}=\alpha_1 * C_{activity}+\beta_1$, the solute activity factor for the acid or sulfur class can be $\lambda_{Acid}=\alpha_2 * C_{activity}+\beta_2$, and the solute activity factor for the other class can be $\lambda_{Other}=\alpha_3 * C_{activity}+\beta_3$.

Linear or Quasi-Linear Relationships for Partition Coefficients

After determining the class definitions for potential solutes, and after determining a functional form for a solute activity coefficient, a general linear or quasi-linear relationship can be developed between a partition coefficient for a solute in a petroleum fraction and water relative to a partition coefficient in octanol and water.

$$P_{solute}(\text{solvent,water})=A * \lambda_{class} * P_{solute}(\text{octanol,water})+B \quad (3)$$

In Equation (3), A represents a scaling factor or slope for the linear or quasi-linear relationship, B represents an intercept value, $\lambda_{class}$ is a scaling factor that is dependent on the class of the solute as described above, and $P_{solute}$(x,water) is a partition coefficient as described above. Note that inclusion of the intercept B is preferred, but is not required.

An example of method for determining $\lambda_{class}$ is provided above. The value of $P_{solute}$(octanol,water) is available for a wide variety of compounds. Additionally, due to the extensive nature of the octanol-water database of partition coefficients, if a partition coefficient is not already available, it can often be estimated, such as by analogy with a known species or by using one of the various methods reported in the literature for estimating an octanol-water partition coefficient based on other physical data. Still another option is to measure the octanol-water partition coefficient in advance for a compound that is planned for use in an extraction, transport, or refining application.

The remaining values in equation (3) are the slope A and the intercept B. It has been determined that these values can be calculated using the solubility (in the form of the solubility constant) of water in the petroleum fraction. The slope A and intercept B can be expressed as a polynomial function of the solubility constant of water in the petroleum fraction. For example, the slope A can be fit as a quadratic polynomial in log $K_{water}$(solvent), while the intercept B can be fit as a linear binomial in log $K_{water}$(solvent). In other words, the slope A and intercept B can be expressed as $$A=a*[\log K_{water}(\text{solvent})]^2+b*\log K_{water}(\text{solvent})+c \quad (4)$$

$$B=f*\log K_{water}(\text{solvent})+g \quad (5)$$

In equations (4) and (5), $K_{water}$(solvent) is the solubility constant of water in the solvent (petroleum fraction), as described previously, an ln is the natural logarithm. Constants a, b, c, f, and g are parameters that are determined by fitting the parameters to data for partition coefficients in petroleum fraction-water systems and octanol-water systems with known (i.e., previously determined) values. It is noted that the constants a, b, c, f, and g are dependent only on the solubility of water in a petroleum fraction or other solvent. Thus, an initial set of constants a, b, c, f, and g could be obtained by fitting data from only a single class of solutes in order to simplify the initial parameter fit process. Additionally, data from solvents other than petroleum fractions may be used in order to provide additional data for known systems. Examples of suitable non-petroleum fraction solvents that can be used for developing the parameter fit include aromatic solvents such as toluene, oxygen containing solvents such as ketones, ethers, alcohols, or esters, hydrocarbon solvents, halogenated solvents, and solvents containing more than one type of functional group such as nitrobenzene. Performing a fit with known systems that includes solutes from all classes may provide improved results. However, given the qualitative nature of the estimated partition coefficients provided by this method, the less complicated parameter fit may be adequate. In other embodiments, other types of polynomial fits can be used for either the slope A or the intercept B.

Figure 1:
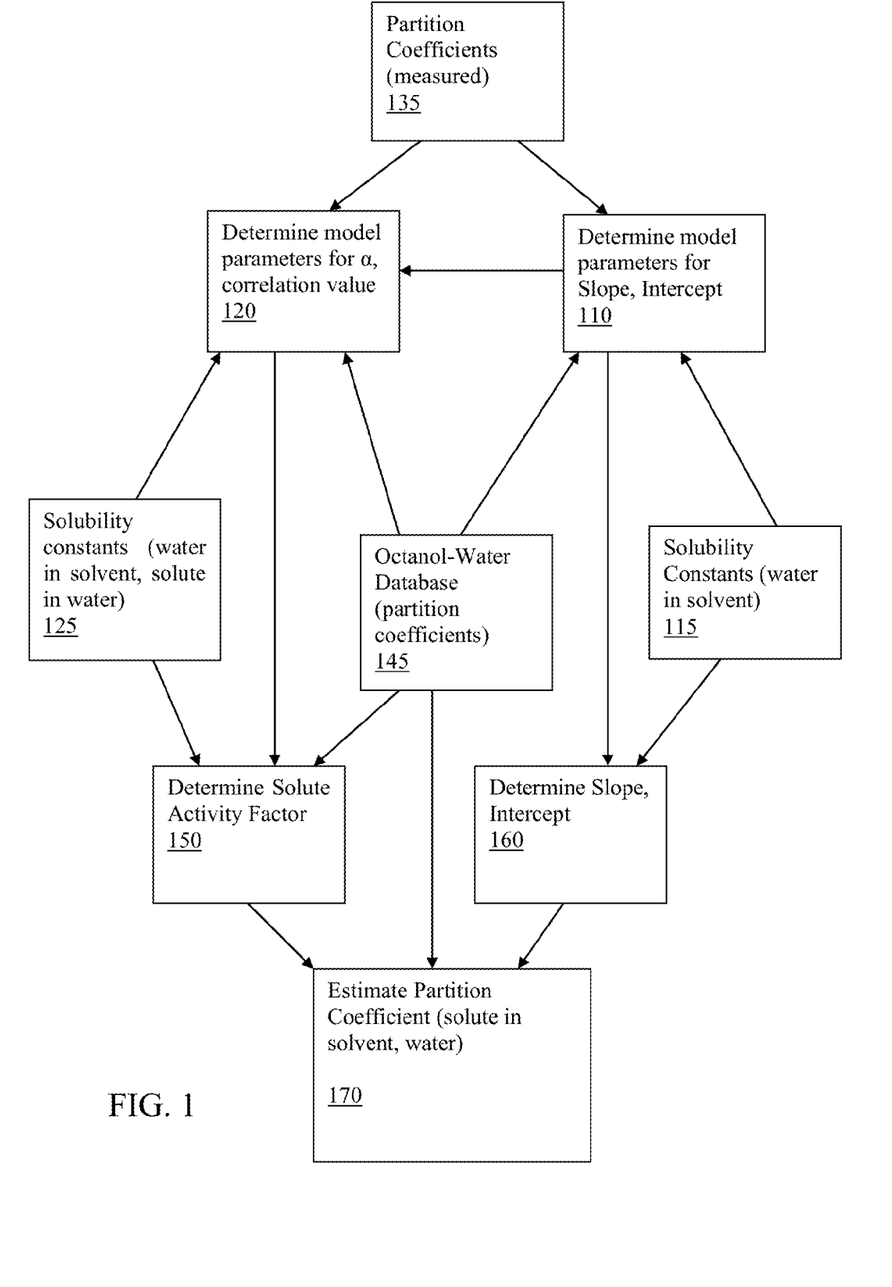
FIG. 1 provides a suitable process flow for estimating a partition coefficient according to the invention.

FIG. 1 shows an example of a flow diagram for developing a model according to the invention. In FIG. 1, a model is constructed starting with various values that are measured or otherwise available. One initial input corresponds to solubility constants for water in a plurality of solvents 115. The solubility constants for water in solvents in combination with solubility constants for various solutes in water 125 provides another input. It is noted that the data in solubility constants 115 and solubility constants 125 will likely have some overlap. The solubility constants for water are represented twice in FIG. 1 to improve the readability of the figure. A third input is data from an octanol-water database or listing 145, which provides partition coefficients for various solutes in octanol versus water. A fourth input is measurements of partition coefficients for solutes in a plurality of other solvent-water systems 135.

Based on the starting inputs, parameters for a model can be fit. One set of parameters corresponds to parameters for determining a slope and optionally an intercept for a linear relationship (or quasi-linear relationship) between octanol-water partition coefficients and partition coefficients for other solvent-water systems. This set of parameters can be determined 110 using solubility constants for water in solvents 115, octanol-water partition coefficients 145, and measured partition coefficient values 135 as inputs. Another set of parameters corresponds to parameters for determining solute activity factor. These parameters include a correlation value and a class-dependent scaling factor α. This set of parameters can be determined 120 using solubility constants 125, octanol-water partition coefficients 145, measured partition coefficients 135, and a parameter set 110 for determining the slope and intercept. Optionally, parameters 110 and parameters 120 can be determined concurrently. After determining model parameters, a partition coefficient for a given combination of solute, solvent, and water can be estimated. Based on a class for the solute, a solute activity factor can be determined 150 using the model parameters 120, solubility constants 125, and an octanol-water partition coefficient from a database or listing 145. A slope and intercept for the estimation can be determined 160 based on the model parameters 110 and solubility constants 115. The partition coefficient for a solute in a solvent-water system can then be estimated based on the slope and intercept values 160, the solute activity factor 150, and the corresponding partition coefficient for octanol and water 145.

Example 2—Demonstration of Methodology

Figure 2:
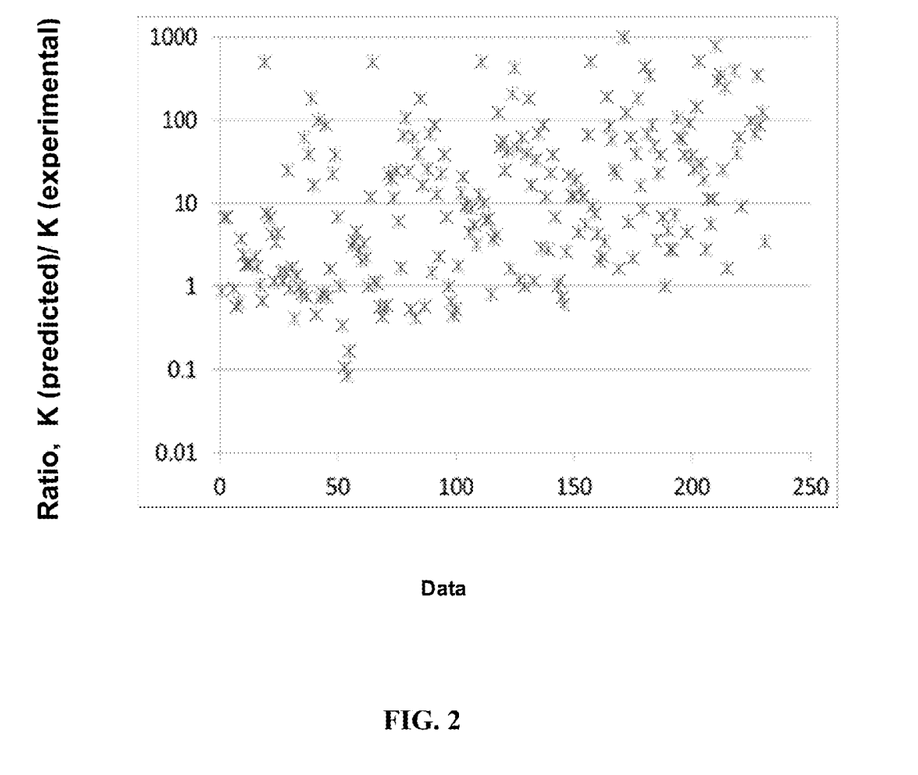
FIG. 2 shows ratios of octanol-water partition coefficients versus measured partition coefficients for various solvent-water systems.

As an initial hypothesis, the partition coefficient for a solute in octanol and water could simply be used directly as an approximation for the partition coefficient for a solute in a petroleum fraction and water. This initial hypothesis was tested by measuring or otherwise obtaining a measured value of the partition coefficient for various solutes in a representative plurality of petroleum fraction-water and other solvent-water systems. FIG. 2 shows a scatter plot of using the octanol-water partition coefficient versus a measured value for various petroleum fraction-water or other solvent-water systems. The vertical axis of FIG. 2 shows a ratio of the partition coefficient values on a log scale, so if the predicted coefficient is identical to the measured coefficient, the data point in FIG. 2 will have a value of 1. The horizontal axis is simply an identifier value for the over 200 solute-petroleum fraction-water or solute-other solvent-water systems that were used in comparing a predicated partition coefficient with a measured partition coefficient. As shown in FIG. 2, for roughly 50% of the solute-solvent-water systems that were investigated, using the octanol-water partition coefficient directly as an estimate for the solvent-water partition coefficient (such as petroleum fraction-water partition coefficient) results in an estimated value that differs from the measured value by more than an order of magnitude. This is indicated by the large number of data values greater than 10 on the logarithmic vertical scale. In fact, a substantial number of values in FIG. 2 show that the octanol-water value differs from the measured value by 2 or even 3 orders of magnitude. This large amount of variation makes it difficult to use the octanol-water partition coefficient value directly as an estimate for a petroleum fraction-water partition coefficient.

Figure 3:
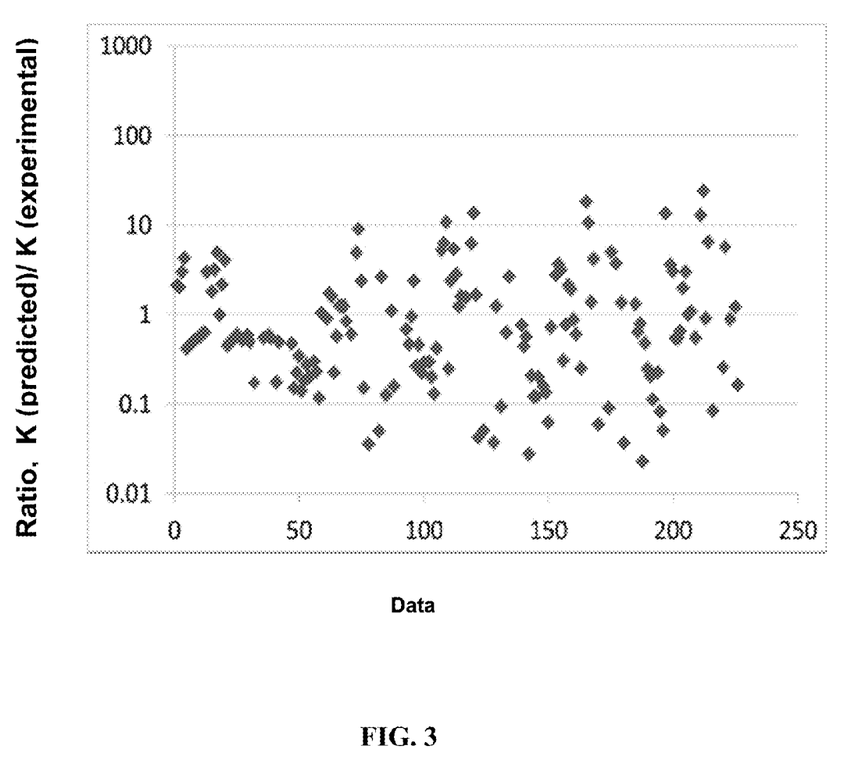
FIG. 3 shows ratios of estimated partition coefficients according to the invention versus measured partition coefficients for various solvent-water systems.

FIG. 3 shows a scatter plot for the same solute-solvent-water systems as in FIG. 2, but with estimated partition coefficients determined according to an example of the invention. As shown in FIG. 3, the partition coefficient estimates provided according to the invention provide a substantial improvement over simply using the octanol-water partition coefficient for a given solute. In FIG. 3, 10% or less of the estimated values differ from the measured value by more than an order of magnitude, and all of the estimated partition coefficient values differ from the measured value by less than 3 orders of magnitude. Additionally, a majority of the predicted partition coefficient values are between 0.2 and 5 times the experimental value.

Figure 4:
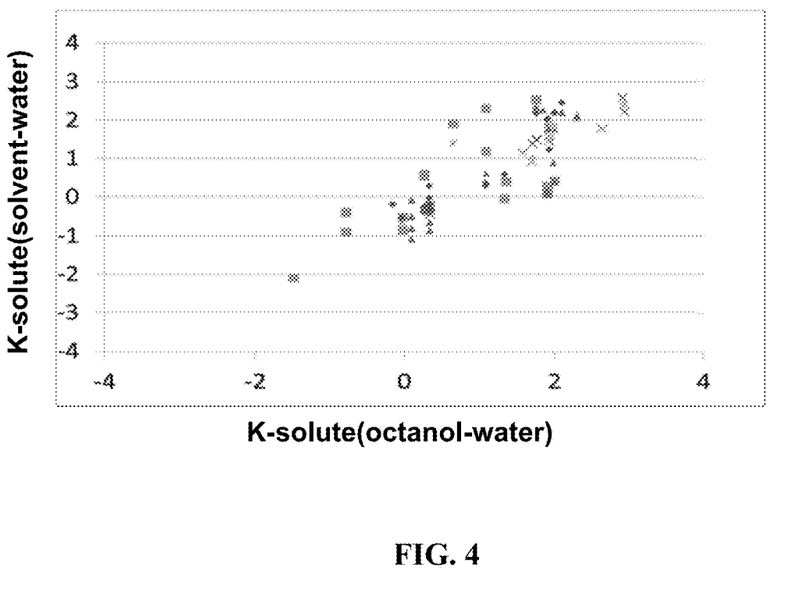
FIG. 4 shows the linear or quasi-linear nature of the relationship between octanol-water partition coefficients and solvent-water partition coefficients for solutes from a single class.

FIG. 4 shows the linearity or quasi-linearity of the relationship between the solvent-water partition coefficient and the octanol-water partition coefficient for solutes within a single solute class (the class containing solutes without nitrogen or acid/sulfur) for various solvents. The data in FIG. 4, which is in the form of a log/log plot, include partition coefficients for various solutes in five different solvents, including solvents that correspond to individual compounds rather than petroleum fractions. As shown in FIG. 4, the solvent-water and octanol-water partition coefficients have a roughly linear relationship. Thus, the format of equation (3) above provides a suitable functional form for approximating this linear relationship.

Figure 5:
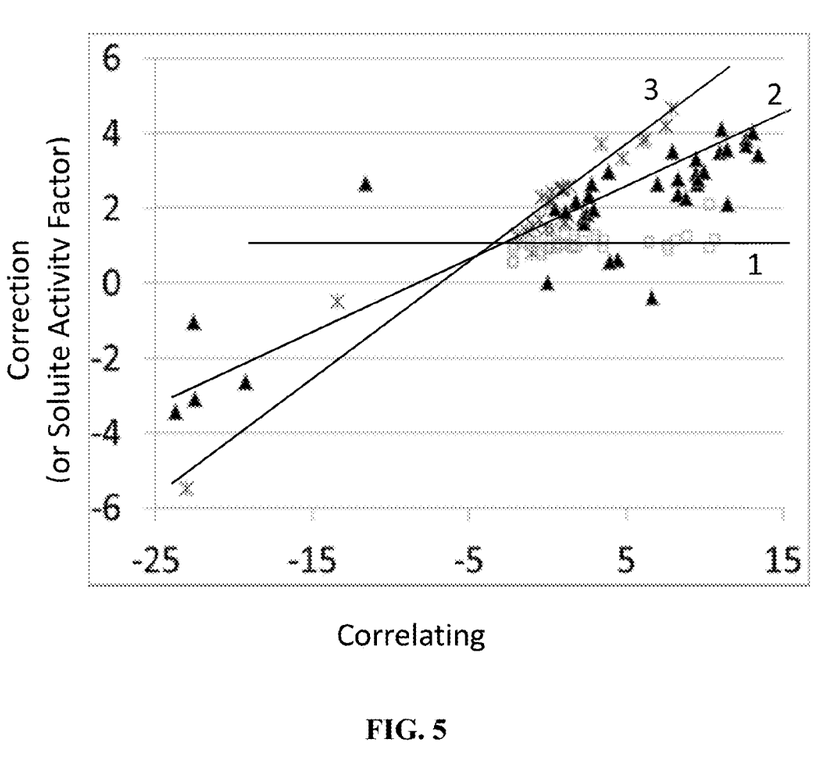
FIG. 5 shows the relationship between solute activity factors and correlating values for various solute classes.

In the description of solute classes described above, a linear relationship was proposed between a solute activity factor and a correlating factor. This solute activity factor provides a correction factor $\lambda$ in equation (3), so that solutes in the nitrogen class and acid/sulfur class have a quasi-linear relationship between solvent-water partition functions and corresponding octanol-water partition functions. FIG. 5 shows an example of the relationships for the three solute classes based on the above definitions. Class 1 corresponds to the acid or sulfur class, class 2 corresponds to the nitrogen class, and class 3 corresponds to other solutes. To generate the data in FIG. 5, measured or previously determined values were obtained for all variables in equation (3) except for the solute activity factor $\lambda$. The partition coefficients for solutes in both solvent-water and octanol-water systems were measured. Parameter fitting was also used for solutes from a single class to develop an initial fit for constants a, b, c, f, and g in equations (4) and (5). The solubility of water in the solvent was then used to generate slope A and intercept B in equation (3). Based on these values, the solute activity factor could be solved for, and this is shown as the vertical axis. The horizontal axis represents the calculated correlating value shown in equation (2). As shown in FIG. 5, all of the classes have an approximately linear relationship. Additionally, for solutes in class 1 corresponding to acids or sulfur-containing compounds, the value in FIG. 5 is approximately 1 for all solutes in the data. This indicates that the α value for class 1 is 1.

Example 2—Comparison with Experimental Data with Oil as Solvent

A model developed in accordance with the above methods was used to determine a predicted partition coefficient for a solute-petroleum fraction-water system reported in the literature. The literature values were reported in Offshore Technology Report OTH 92 385, which was published by the Health and Safety Executive of Great Britain in 1993. In the report, the partitioning of $H_2S$ between a North Sea crude oil and water was investigated. A range of water solubilities in the crude oil (petroleum fraction) were provided in the report. An experimental determination of the partition coefficient was also performed. The experimental value for the log of the partition coefficient was 0.612, which corresponds to a partition coefficient of 4.09 for $H_2S$ in the crude oil.

To determine the predicted value according to the invention, a prior fit for the a, b, c, f, and g parameters was used. Because $H_2S$ contains sulfur, the solute was assigned to class 1. Thus, the solute activity scaling factor was set to 1.0. The solute activity factor was determined based on the solubility of $H_2S$ in water, the reported solubility of water in the crude oil, and the partition coefficient for $H_2S$ in octanol and water, and the scaling factor of 1.0. Several values for the solubility of water in the crude oil were available. As a result, the values 55 gmol/m³ and 200 gmol/m³ were used as nominal lower and upper bounds. Both values were used to determine a solute activity factor, leading to solute activity factors of 0.408 or −0.488, respectively. The above values also allowed for calculation of a slope A and intercept B. The 55 gmol/m³ value resulted in a slope A of 1.127 and intercept B of −1.329 for equation (3). The 200 gmol/m³ value resulted in a slope A of 1.123 and an intercept B of −0.823. These values were then used in equation (3) to generate predicted values for the partition coefficient. The water solubility of 55 gmol/m³ resulted in a predicted partition coefficient of 1.96 (log K=0.29) while the water solubility of 200 gmol/m³ resulted in a predicted partition coefficient of 6.25 (log K=0.80). The upper and lower bound values can be compared to the experimental value of 4.09 (log K experimental=0.612) for $H_2S$ in the crude oil mentioned above. As shown by the range of predicted values, the method according to the invention provided an estimate of the log of the partition coefficient between about 0.2 and 5 times the experimental value. For comparison, a literature value for the partition coefficient of $H_2S$ in octanol-water was 27.5 (log K=1.44).

In another example, a partition coefficient was predicted according to the invention for a system reported in the literature consisting of phenol as a solute, a Miller (North Sea) crude oil, and water. Data for this phenol-crude oil-water system was discussed in a report published in Geochimica et Cosmochimica, Vol. 61, pg 4393 (1997). The experimental value for the log of the partition coefficient of phenol was determined as 0.238, which corresponds to a partition coefficient 1.72. Because phenol is acidic, the solute was also assigned to class 1. Because the crude oil is also a North Sea crude, the same nominal bounding values for the solubility of water in the crude oil were used. As a result, the slope and intercept values A, B are the same as in the previous example, with slope A of 1.127 or 1.123 and intercept B of −1.329 or −0.823 for equation (3). The solubility of phenol in water is 853 gmol/m³. The solute activity factor was determined based on the solubility of phenol in water, the solubility of water in the crude oil, and the partition coefficient for phenol in octanol and water, and a previously fit scaling factor of 1.0 for the relationship between the solute activity factor and correlating value for class 1. Thus, the solute activity scaling factor was set to 1. Several values for the solubility of water in the crude oil were available. Both nominal water solubility in crude oil values were also used to determine a solute activity factor for phenol partitioning, leading to solute activity factors of 1.877 or 0.993, respectively. These values were then used in equation (3) to generate predicted values for the partition coefficient. The water solubility of 55 gmol/m³ resulted in a predicted partition coefficient of 2.0 (log K=0.30). The experimental value for the partition coefficient is 1.72 (log K=0.24). For comparison, a literature value for the partition coefficient of phenol in octanol-water was 28.8 (log K=1.45), which is more than an order of magnitude different from the experimental value.

In still another example, a partition coefficient was estimated for a system consisting of caprolactam as a solute, chloroform as a solvent, and water. Data regarding the caprolactam-chloroform-water system has been reported in U.S. Pat. No. 6,191,274. The experimental value for the log of the partition coefficient of phenol was determined as −0.13 which corresponds to a partition coefficient 0.74. Caprolactam contains nitrogen and therefore, the solute was also assigned to class 2. The solubility of caprolactam in water is 40353 gmol/m³. The solubility of water in chloroform is 68.4 gmol/m³. These values were used to determine a solute activity factor for caprolactam partitioning, leading to a solute activity factor of −33.57. The solubility of water in chloroform was also used to determine a slope A of 1.13 and an intercept B of −1.24. These values were then used in equation (3) to generate an estimated value for the partition coefficient of 0.826 (log K=−0.083). The corresponding experimental partition coefficient is 0.74 (log K=−0.131). Once again, the method according to the invention provided an estimate of the partition coefficient between about 0.2 and 5 times the experimental value.

ADDITIONAL EMBODIMENTS

Embodiment 1

A method for predicting a partition coefficient for a solute between a petroleum fraction and water, comprising: selecting a solute class for a solute; determining a solubility constant of water in a petroleum fraction; calculating a solute activity factor based on the solubility constant of water in the petroleum fraction, a solubility constant of the solute in water, a partition coefficient for the solute in octanol and water, and the solute class; and predicting a partition coefficient for the solute in the petroleum fraction and water based on the partition coefficient for the solute in octanol and water, the solute activity factor, and a scaling factor based on the solubility constant of water in the petroleum fraction.

Embodiment 2

A method for predicting a partition coefficient for a solute between a solvent and water, comprising: identifying a plurality of solute classes; fitting parameters for determining a slope in a linear or quasi-linear relationship between a partition coefficient in a solvent and water and a corresponding partition coefficient in octanol and water, the parameters for determining the slope corresponding to coefficients in a polynomial expression based on a solubility constant of water in the solvent, the fitting of parameters being based on a plurality of solvent-water systems; selecting a solute class for a solute; determining a solubility constant of water in a solvent, the solvent being different from solvents in the plurality of solvent-water systems; calculating a solute activity factor based on the solubility constant of water in the solvent, a solubility constant of the solute in water, a partition coefficient for the solute in octanol and water, and the solute class; and predicting a partition coefficient for the solute in the solvent and water based on the partition coefficient for the solute in octanol and water, the solute activity factor, and a scaling factor based on the solubility constant of water in the solvent.

Embodiment 3

A method according to embodiment 2, wherein the polynomial expression is a quadratic polynomial.

Embodiment 4

A method according to embodiments 2 or 3, wherein fitting parameters further comprises fitting parameters for determining an intercept value for the linear or quasi-linear relationship, the parameters for determining the intercept value corresponding to coefficients in a polynomial expression based on a solubility constant of water in the solvent, the fitting of parameters being based on a plurality of solvent-water systems.

Embodiment 5

A method according to any of embodiments 1-4, wherein the solubility constant of water in the petroleum fraction or solvent is determined by measuring a solubility of water in the petroleum fraction or solvent.

Embodiment 6

A method according to any of embodiments 1-5, wherein the scaling factor based on the solubility constant of water in the petroleum fraction corresponds to a slope for a linear or quasi-linear relationship between the partition coefficient for the solute in the petroleum fraction and water and the partition coefficient for the solute in octanol and water.

Embodiment 7

A method according to any of embodiments 1-6, wherein the solute activity factor comprises a scaling factor based on the solute class and a correlation value, the correlation value being defined by $$C_{activity} = \frac{\ln\left(\frac{K_{solute}(\text{water})}{K_{water}(\text{solvent})}\right)}{\log P_{solute}(\text{octanol, water})}$$

where $C_{activity}$ is the correlation value, $K_{solute}(\text{water})$ is the solubility constant of the solute in water, $K_{water}(\text{solvent})$ is the solubility constant of water in the petroleum fraction, and $P_{solute}(\text{octanol,water})$ is the partition coefficient of the solute in octanol and water.

Embodiment 8

A method according to any of embodiments 1-7, wherein the partition coefficient for the solute in the petroleum fraction and water is predicted using the relationship $$P_{solute}(\text{solvent,water}) = A^* \lambda_{class}^* P_{solute}(\text{octanol,water})$$

where $P_{solute}(\text{solvent,water})$ is the partition coefficient of the solute in the petroleum fraction and water, $P_{solute}(\text{octanol, water})$ is the partition coefficient of the solute in octanol and water, A is the scaling factor based on the solubility constant of water in the petroleum fraction, and $\lambda_{class}$ is $\zeta^* C_{activity}$, with the value of a being dependent on the solute class, and wherein the scaling factor A corresponds to $$A = \alpha^* [\log K_{water}(\text{solvent})]^2 + b^* \log K_{water}(\text{solvent}) + c$$

where $K_{water}(\text{solvent})$ is the solubility constant of water in the petroleum fraction and a, b, and c are parameters determined based on parameter fitting using a plurality of solvents.

Embodiment 9

A method according to any of embodiments 1-7, wherein the partition coefficient for the solute in the petroleum fraction and water is predicted using the relationship $$P_{solute}(\text{solvent,water}) = A^* \lambda_{class}^* P_{solute}(\text{octanol,water}) + B$$

where $P_{solute}(\text{solvent,water})$ is the partition coefficient of the solute in the petroleum fraction and water, $P_{solute}(\text{octanol, water})$ is the partition coefficient of the solute in octanol and water, A is the scaling factor based on the solubility constant of water in the petroleum fraction, B is a factor based on the solubility constant of water in the petroleum fraction, and $\lambda_{class}$ is $\alpha^* C_{activity}$, with the value of $\alpha$ being dependent on the solute class, and wherein the scaling factor B corresponds to $$B = f^* \log K_{water}(\text{solvent}) + g$$

where $K_{water}(\text{solvent})$ is the solubility constant of water in the petroleum fraction and f and g are parameters determined based on parameter fitting using a plurality of solvents.

Embodiment 10

A method according to any of embodiments 1-9, wherein the petroleum fraction or solvent consists essentially of oil derived from a mineral source.

Embodiment 11

A method according to any of embodiments 1-10, wherein the solute class is selected from a first class for solutes containing nitrogen, a second class for solutes containing sulfur, an acidic functional group, or a hydroxyl functional group, and a class for solutes not assigned to the first class or second class.

Embodiment 12

A method according to embodiment 11, wherein a solute assigned to the first class for solutes containing nitrogen is not considered for assignment to the second class for solutes containing sulfur or an acidic functional group.

Embodiment 13

A method according to any of embodiments 1-12, wherein the solute is a corrosion inhibitor, a scale inhibitor, or a compound for inhibiting formation of gas hydrates.

What is claimed is:

1. A method for predicting a partition coefficient for a solute between a petroleum fraction and water, comprising:
   selecting a solute class for a solute;
   obtaining a sample of a petroleum fraction;
   determining a solubility constant of water in the petroleum fraction;
   calculating a solute activity factor based on the solubility constant of water in the petroleum fraction, a solubility constant of the solute in water, a partition coefficient for the solute in octanol and water, and the solute class; wherein the solubility constant of water in the petroleum fraction is determined by measuring a solubility of water in the petroleum fraction; wherein the solute activity factor comprises a scaling factor based on the solute class and a correlation value, the correlation value being defined by $$C_{activity} = \frac{\ln\left(\frac{K_{solute}(\text{water})}{K_{water}(\text{solvent})}\right)}{\log P_{solute}(\text{octanol, water})}$$

where $C_{activity}$ is the correlation value, $K_{solute}(\text{water})$ is the solubility constant of the solute in water, $K_{water}(\text{solvent})$ is the solubility constant of water in the petroleum fraction, and $P_{solute}(\text{octanol,water})$ is the partition coefficient of the solute in octanol and water;
   predicting a partition coefficient for the solute in the petroleum fraction and water based on the partition coefficient for the solute in octanol and water, the solute activity factor, and a scaling factor based on the solubility constant of water in the petroleum fraction; and
   adding the solute to the petroleum fraction based on the predicted partition coefficient.

2. The method of claim 1, wherein the scaling factor based on the solubility constant of water in the petroleum fraction corresponds to a slope for a linear or quasi-linear relationship between the partition coefficient for the solute in the petroleum fraction and water and the partition coefficient for the solute in octanol and water.

3. The method of claim 1, wherein the partition coefficient for the solute in the petroleum fraction and water is predicted using the relationship $$P_{solute}(\text{solvent,water}) = A * \lambda_{class} * P_{solute}(\text{octanol,water})$$

where $P_{solute}(\text{solvent,water})$ is the partition coefficient of the solute in the petroleum fraction and water, $P_{solute}(\text{octanol,water})$ is the partition coefficient of the solute in octanol and water, A is the scaling factor based on the solubility constant of water in the petroleum fraction, and $\lambda_{class}$ is $\alpha * C_{activity}$, with the value of a being dependent on the solute class.

4. The method of claim 3, wherein the scaling factor A corresponds to $$A = a * [\log K_{water}(\text{solvent})]^2 + b * \log K_{water}(\text{solvent}) + c$$

where $K_{water}(\text{solvent})$ is the solubility constant of water in the petroleum fraction and a, b, and c are parameters determined based on parameter fitting using a plurality of solvents.

5. The method of claim 1, wherein the partition coefficient for the solute in the petroleum fraction and water is predicted using the relationship $$P_{solute}(\text{solvent,water}) = A * \lambda_{class} * P_{solute}(\text{octanol,water}) + B$$

where $P_{solute}(\text{solvent,water})$ is the partition coefficient of the solute in the petroleum fraction and water, $P_{solute}(\text{octanol,water})$ is the partition coefficient of the solute in octanol and water, A is the scaling factor based on the solubility constant of water in the petroleum fraction, B is a factor based on the solubility constant of water in the petroleum fraction, and $\lambda_{class}$ is $\alpha * C_{activity}$, with the value of a being dependent on the solute class.

6. The method of claim 5, wherein the scaling factor B corresponds to $$B = f * \log K_{water}(\text{solvent}) + g$$

where $K_{water}(\text{solvent})$ is the solubility constant of water in the petroleum fraction and f and g are parameters determined based on parameter fitting using a plurality of solvents.

7. The method of claim 1, wherein the petroleum fraction consists essentially of oil derived from a mineral source.

8. The method of claim 1, wherein the solute class is selected from a first class for solutes containing nitrogen, a second class for solutes containing sulfur, or an acidic functional group, or a hydroxyl functional group, and a third class for solutes not assigned to the first class or second class.

9. The method of claim 8, wherein a solute assigned to the first class for solutes containing nitrogen is not considered for assignment to the second class for solutes containing sulfur or an acidic functional group.

10. The method of claim 1, wherein the solute is a corrosion inhibitor, a scale inhibitor, or a compound for inhibiting formation of gas hydrates.

11. A method for predicting a partition coefficient for a solute between a solvent and water, comprising:
    identifying a plurality of solute classes;
    fitting parameters for determining a slope in a linear or quasi-linear relationship between a partition coefficient in a solvent and water and a corresponding partition coefficient in octanol and water, the parameters for determining the slope corresponding to coefficients in a polynomial expression based on a solubility constant of water in the solvent, the fitting of parameters being based on a plurality of solvent-water systems;
    selecting a solute class for a solute;
    determining a solubility constant of water in a solvent, the solvent being different from solvents in the plurality of solvent-water systems;
    calculating a solute activity factor based on the solubility constant of water in the solvent, a solubility constant of the solute in water, a partition coefficient for the solute in octanol and water, and the solute class; wherein the solute activity factor comprises a scaling factor based on the solute class and a correlation value, the correlation value being defined by $$C_{activity} = \frac{\ln\left(\frac{K_{solute}(\text{water})}{K_{water}(\text{solvent})}\right)}{\log P_{solute}(\text{octanol, water})}$$

where $C_{activity}$ is the correlation value, $K_{solute}(\text{water})$ is the solubility constant of the solute in water, $K_{water}(\text{solvent})$ is the solubility constant of water in the solvent, and $P_{solute}(\text{octanol,water})$ is the partition coefficient of the solute in octanol and water; and
    predicting a partition coefficient for the solute in the solvent and water based on the partition coefficient for the solute in octanol and water, the solute activity factor, and a scaling factor based on the solubility constant of water in the solvent; and adding the solute to the solvent based on the predicted partition coefficient.

12. The method of claim 11, wherein the solvent comprises a petroleum fraction.

13. The method of claim 11, wherein the polynomial expression is a quadratic polynomial.

14. The method of claim 11, wherein fitting parameters further comprises fitting parameters for determining an intercept value for the linear or quasi-linear relationship, the parameters for determining the intercept value corresponding to coefficients in a polynomial expression based on a solubility constant of water in the solvent, the fitting of parameters being based on a plurality of solvent-water systems.

15. The method of claim 11, wherein the solute class is selected from a first class for solutes containing nitrogen, a second class for solutes containing sulfur, or an acidic functional group, or a hydroxyl functional group, and a third class for solutes not assigned to the first class or second class.

16. The method of claim 11, wherein partition coefficient for the solute in the solvent and water is predicted using the relationship $$P_{solute}(\text{solvent,water}) = A * \lambda_{class} * P_{solute}(\text{octanol,water}) + B$$

where $P_{solute}$(solvent,water) is the partition coefficient of the solute in the solvent and water, $P_{solute}$(octanol,water) is the partition coefficient of the solute in octanol and water, A is the scaling factor based on the solubility constant of water in the solvent, B is a factor based on the solubility constant of water in the solvent, and λclass is α*Cactivity, with the value of a being dependent on the solute class.

17. The method of claim 16, wherein the scaling factor A corresponds to $$A = a*[\log K_{water}(\text{solvent})]^2 + b*\log K_{water}(\text{solvent}) + c$$

where $K_{water}$(solvent) is the solubility constant of water in the solvent and a, b, and c are parameters determined based on the fitting of parameters.

18. The method of claim 16, wherein the scaling factor B corresponds to $$B = f*\log K_{water}(\text{solvent}) + g$$

where $K_{water}$(solvent) is the solubility constant of water in the solvent and f and g are parameters determined based on the fitting of parameters.

* * * * *